United States Patent
Colombo (10) Patent No.: US 10,974,037 B2
(45) Date of Patent: Apr. 13, 2021

(54) DEVICE FOR THE PREPARATION AND APPLICATION OF A MEDICAL SUBSTANCE

(71) Applicant: NEX MEDICAL ANTISEPTICS S.R.L., Casorezzo (IT)

(72) Inventor: Aldo Colombo, Cerro Maggiore (IT)

(73) Assignee: NEX MEDICAL ANTISEPTICS S.R.L., Casorezzo (IT)

( * ) Notice: Subject to any disclaimer, the term of this patent is extended or adjusted under 35 U.S.C. 154(b) by 547 days.

(21) Appl. No.: 15/538,204

(22) PCT Filed: Dec. 21, 2015

(86) PCT No.: PCT/EP2015/080723
§ 371 (c)(1),
(2) Date: Jun. 21, 2017

(87) PCT Pub. No.: WO2016/102429
PCT Pub. Date: Jun. 30, 2016

(65) Prior Publication Data
US 2017/0348517 A1 Dec. 7, 2017

(30) Foreign Application Priority Data
Dec. 23, 2014 (IT) .......................... BS2014A000218

(51) Int. Cl.
*A61M 35/00* (2006.01)
*A61F 13/40* (2006.01)
*A47K 7/02* (2006.01)

(52) U.S. Cl.
CPC ........... *A61M 35/003* (2013.01); *A47K 7/028* (2013.01); *A61M 35/006* (2013.01)

(58) Field of Classification Search
CPC .................... A61M 35/003; A61M 35/006
See application file for complete search history.

(56) References Cited

U.S. PATENT DOCUMENTS 3,802,604 A * 4/1974 Morane ................. B65D 51/28
 222/83
4,507,111 A * 3/1985 Gordon ................. A47K 7/028
 401/134
(Continued)

FOREIGN PATENT DOCUMENTS

WO 2007018541 A1 2/2007
WO 2011018621 A2 2/2011

OTHER PUBLICATIONS

Search Report of PCT/EP2015/080723 dated Apr. 26, 2016.

*Primary Examiner* — Ariana Zimbouski
(74) *Attorney, Agent, or Firm* — Silvia Salvadori, P.C.; Silvia Salvadori (57) ABSTRACT

The present invention regards an applicator device for the preparation and application of at least one medical substance, preferably a coloured liquid, comprising: a hollow chamber having a hosting end and an opposite distal end in communication with means for contact with the patient; a cartridge slidingly inserted into said hollow chamber, containing at least one first medical substance, and having a first end external to the hollow chamber, and a second end completely inserted into the hollow chamber; a breaking means positioned at the distal end, capable of establishing a fluid communication between the internal of the cartridge and the means for contact with the patient; said second end being sealed by a filled double layer closure system containing at least one second substance, preferably coloured, mixable and/or soluble with the first medical substance contained in the cartridge.

13 Claims, 5 Drawing Sheets

(56) References Cited

U.S. PATENT DOCUMENTS

2003/0040141 A1     2/2003   Crane
2014/0205360 A1*   7/2014   Dokken .............. A61M 35/006
                                                                                                                                                                                              401/263

* cited by examiner

DEVICE FOR THE PREPARATION AND APPLICATION OF A MEDICAL SUBSTANCE

This application is a U.S. national stage of PCT/EP2015/080723 filed on 21 Dec. 2015, which claims priority to and the benefit of Italian Application No. BS2014A000218, filed on 23 Dec. 2014, the contents of which are incorporated herein by reference in their entireties.

FIELD OF APPLICATION

The present invention generally refers to an applicator device for the preparation and application of a medical substance, preferably coloured, for example for cutaneous administration.

PRIOR ART

During surgery preparation steps, or before infusion of liquids or intravenous administration of drugs (for example before inserting a central venous catheter) or simple injection, there often arises the need of performing one or more preliminary disinfection operations on the skin of the area in question, alongside the optical identification thereof, typically by means of a dyeing substance. Therefore, it is crucial to have applicators and/or cutaneous administration means capable of allowing both the disinfection and dyeing of the skin in proximity of the body area meant to be subject of the intervention. Regarding this, medical antiseptic and dyeing substances that can be utilised mutually combining them when required or utilising them separately by means of two different applicators are known. However, the latter method reveals some objective drawbacks such as, for example, the need to have at least two applicators (one for the medical substance and one for the dyeing substance), the overall dimension observable when using two different applicators as well as the practicality of the operations in question. Therefore, applicator devices for medical purposes allow applying several medical substances contained therein, useable for cutaneous treatments, for example, antiseptic substances, disinfectants or the like have been developed.

Generally, devices known in the prior art have a chamber, containing the medical substance to be applied, having an openable end inserted into a hollow body, typically cylindrical, providing a medical substance following the breakage of the chamber or the openable end thereof.

U.S. Pat. No. 4,507,111 describes a medical applicator provided with a cartridge, containing a medical substance, slidably inserted into a tubular container which also serves as a handle, at whose end there is a sponge. The device is characterised in that it has a dispensing chamber inserted into the sponge connected to the tubular container and in fluid communication with the interior of the cartridge. Thus, following the activation of the device, the medical substance passes from the cartridge to the sponge, through the dispensing chamber. However, said system does not allow the optimal mixing of the medical substance for example with a dyeing substance, and the impregnation of the sponge may not be optimal in that the substance released from the dispensing chamber may remain confined in the area surrounding said chamber, creating an impregnation gradient between the centre of the sponge and the ends thereof.

WO2007/076121 discloses an applicator for medical liquids characterised in that it has a cartridge within which there is present a sealed glass ampoule containing the medical substance to be applied. When required, said ampoule is broken by a breaking system present in the device so that the medical substance may flow towards the external and thus come to contact with the surface to be treated. It will be clear to the person skilled in the art that the use of such glass ampoule system may reveal drawbacks mainly related to the fragility of the material in question which, for example during transportation or preparation, may break or crack inadvertently. In addition, following the activation of the device, the broken glass ampoule may generate fragments or small residue material that may flow together with the medical substance and may come to contact with the surface to be treated.

In addition, the use of glass ampoules creates various complications as regards handling and disposal of hospital wastes.

WO2004083905 refers to a device for the application of a fluid containing an ampoule system similar to the one described in WO2007/076121 mentioned above, also containing a filter on which a dyeing substance is impregnated. Said filter is arranged in the applicator in an intermediate position between the ampoule and a porous means which serves as a sponge, so that, following the breakage of the ampoule, the medical substance is made to flow towards the sponge, by passing through the filter which thus releases the dyeing substance and creates the final coloured medical substance which is applied. Besides the aforementioned drawbacks related to the use of a glass ampoule, the device requires an additional filter loading operation and subsequent positioning thereof inside the device so as to avoid the occurrence of undesired lateral leakage of the medical substance, and so that the entire medical substance released by the broken ampoule actually passes through the filter. Besides requiring particular implementation solutions, all this implies that part of the dyeing substance sticks to the walls of the filter and thus does not allow entirely dyeing the out-flowing medical substance. This means that should there arise the need to use precise dosages of the dyeing substance (for example so as to obtain determined dyeing intensity), the prior art device may not be optimal due to the fact that the amount of dyeing substance loaded onto the filter does not correspond to the amount of dyeing substance actually mixed with the medical substance. In addition, such filter system only applies to solid substances in form of powder.

Thus, the technical problem on which the present invention is based is to provide a medical substance, preferably coloured and dyeing, having structural and functional characteristics such to overcome the aforementioned drawbacks related to the prior art, and which is also easy to use for health operators and have low production costs.

SUMMARY OF THE INVENTION

In a first aspect, the invention refers to an applicator device for the preparation and application of at least one medical substance, preferably a coloured and dyeing substance, for example for the cutaneous application of an antiseptic agent, comprising: a hollow chamber, preferably cylindrical, having a hosting end and an opposite distal end carrying a means for contact with the patient, for example in form of a sponge or spout, a cartridge slidingly inserted into said hollow chamber by means of a hosting end, containing at least one first medical substance, and having a first upper end external to the hollow chamber, and a second lower end completely inserted into the hollow chamber, said second lower end being characterised in that it is hermetically closed by a filled double layer closure system, containing at least one second substance mixable and/or soluble with the first medical substance contained in the cartridge. The end external to the hollow chamber is instead shaped so that it is possible to exert pressure thereon, typically using a finger, thus allowing the cartridge to slide into the hollow chamber. Advantageously, the applicator device of the invention allows performing a single and continuous movement of the cartridge, without requiring actuating intermediate block positions, for example required to perform the additional mixing steps, like in similar devices of the prior art. As a matter of fact, regarding this, the breaking means and the double layer closure system make the present invention easy to implement and obtain, thus guaranteeing optimal performance in terms of carrier and mixing capacity of the two components (for example an antiseptic and dyeing substance).

The present applicator device, may also comprise an additional element such as a flange, a finger grip or the like, positioned in proximity of the upper end of the cartridge and adapted to increase the grip and/or ease of use. During the operation of the device, the cartridge, and in particular the lower end carrying the double layer closure system, is made to slide into the cylindrical chamber, towards a breaking system positioned at the distal end of the chamber, up to causing the tearing of the filled double layer closure system and lead to the mixing of the substances respectively contained in the cartridge and in the filled double layer. As above indicated, the mixing of the two substances occurs through a single sliding movement of the cartridge, up to the breaking of the filled double layer. The breaking means develops in a substantially orthogonal fashion towards the internal of the hollow chamber starting from the distal end of the latter, and it is shaped so as to be able to break the double layer closure system by pressing the latter, and creating a fluid communication between the interior of the cartridge and the means of contact with the patient. Thus, the breaking means may be in form of a hollow cylinder which extends into the hollow chamber (in inoperative conditions of the device) in a substantially orthogonal fashion starting from the distal end of said chamber, and which is capable of creating a fluid communication between the interior of the cartridge and the element of contact with the patient, upon the activation of the applicator device. The fluid communication that is generated allows the carrying of the mixture through the contact means, preferably in form of a sponge, immediately after the breakage of the double layer and the relative mixing of the components, substantially without requiring further preferential paths of the mixture to be applied, or further components.

In the present applicator device, the hollow chamber and the cartridge have mutually integrally joined dimensions and/or diameters, i.e. capable of allowing the sliding of the cartridge into the hollow chamber in a fluid fashion, substantially preventing the unwanted lateral leakage of the medical substance, preferably liquid, contained in the cartridge. The filled double layer closure system may contain different amounts of at least one solid, liquid or gel substance therein, for example a second additional medical substance or, preferably and according to a preferred embodiment, a dyeing substance, soluble in the first medical substance contained in the cartridge. Said closure system is obtained by joining two layers of film material, so that a first layer and the content are within the cartridge, whilst the second closure layer serves as a cap for sealing the cartridge. Thus, the cartridge does not require additional closure components, such as sealing membranes or closure caps, in that the filler double layer itself serves as a sealing cap capable of keeping the properties of the substances contained in the applicator and the required sterility levels unvaried. Therefore, not only does the filled double layer allow sealing the end of the cartridge keeping the characteristics, for example the sterility of the substance contained therein, unvaried, but it also allows the tearing thereof by the breaking means in a simple and efficient manner, guaranteeing the complete mixing of the contents thereof and the subsequent carrying of the obtained mixture to the contact means. In addition, the shape, dimensions and amount of substance enclosable in the double layer may be calibrated and modified depending on the type of substance intended to be contained therein and/or the type of combination intended to be obtained with the first medical substance contained in the cartridge. In addition, it should be observed that contrary to the systems of the prior art providing for use of filters or other solid media, the present double layer closure system is easy to obtain, does not require absorption operations or intermediate mixing steps and, above all, it allows releasing the entire content of the filler double layer, substantially without leaving unutilised or residual product.

Lastly, the element of contact with the patient of the present device is connected to the lower end of the hollow chamber and in fluid communication with the cartridge through the previously described breaking means. Basically, the contact element may be made of a material capable of being impregnated with the medical substance prepared with the present device, or it can be shaped to form a spout and/or device of the roll-on type, capable of being placed at contact with the skin to be treated, and homogeneously distribute the medical substance prepared using the present device. Advantageously, the present invention allows preparing and administering medicaments in the moment of need, by using the applicator device of the invention which allows mixing a first medical substance, for example antiseptic, with a second substance, for example in form of medical dyeing substance, as described further in detail hereinafter.

The operation of the present dispensing device occurs by exerting pressure on the upper end of the cartridge, external to the hollow chamber, so that the cartridge slides in the latter, preferably in a fluid and continuous fashion. Such movement will be prolonged until the filled double layer closing the second lower end of the cartridge is torn by the breaking means, thus allowing the immediate mixing of the first medical substance, contained in the cartridge, with the second substance, contained in the filled double layer system. Basically, the cartridge is made to slide all the way in a single movement, stopping after contact with the distal end of the hollow chamber, carrying the breaking means, which at this point will be inserted in the cartridge. Such configuration facilitates the mixing of the content of the filled double layer (for example dyeing powder) with the first medical substance contained in the cartridge, especially due to the turbulence generated by the outflow of said medical substance. Advantageously, the breaking means also generates a fluid communication between the interior of the cartridge and the element of contact with the patient, thus making the present device operative without requiring preferential paths or additional carrier components.

The device for the preparation and application of a medical substance of the invention can be particularly appreciated in pre-operation contexts for example for the identification and simultaneous disinfection of the cutaneous part of body areas to be subjected e.g. to surgery. Thanks to its ease of use and versatility, the present device can also be used for skin treatments, generally, for example in treating wounds, lesions or even for applying medicaments and/or drugs on the patient's skin.

Further characteristics and advantages of the device for applying medical substances according to the invention shall be apparent from the description, outlined hereinafter, of some embodiments provided solely by way of non-limiting example with reference to the attached drawings.

BRIEF DESCRIPTION OF THE DRAWINGS

FIG. 4 represents a front view of the detail of the device illustrated in FIG. 3a.

DETAILED DESCRIPTION

The present medical device allows preserving at least one first medical substance, preferably antiseptic and liquid, and at least one second substance, preferably a powder dyeing substance, in the same device, without said substances inadvertently coming to contact or being in direct communication with each other. Thus, the chemical characteristics of the two substances may remain unaltered over the time without affecting each other. When required, the device may be actuated by sliding the cartridge within the hollow chamber, allowing the mixing of the two substances, and the subsequent administration, typically cutaneous, of the thus prepared medical substance. Regarding this, it should be observed that the mixing between the medical substance contained in the cartridge and the one in the filled double layer occurs only after activating the applicator as described herein.

With reference to FIGS. 1-4, a first embodiment of the applicator device of the invention for applying a liquid medical substance, particularly indicated for cutaneous treatment, is generally identified with 1. In such first embodiment, the applicator device 1 is provided by a device for the preparation and ensuing cutaneous administration of a coloured and dyeing solution of at least one antiseptic substance.

Figure 1:
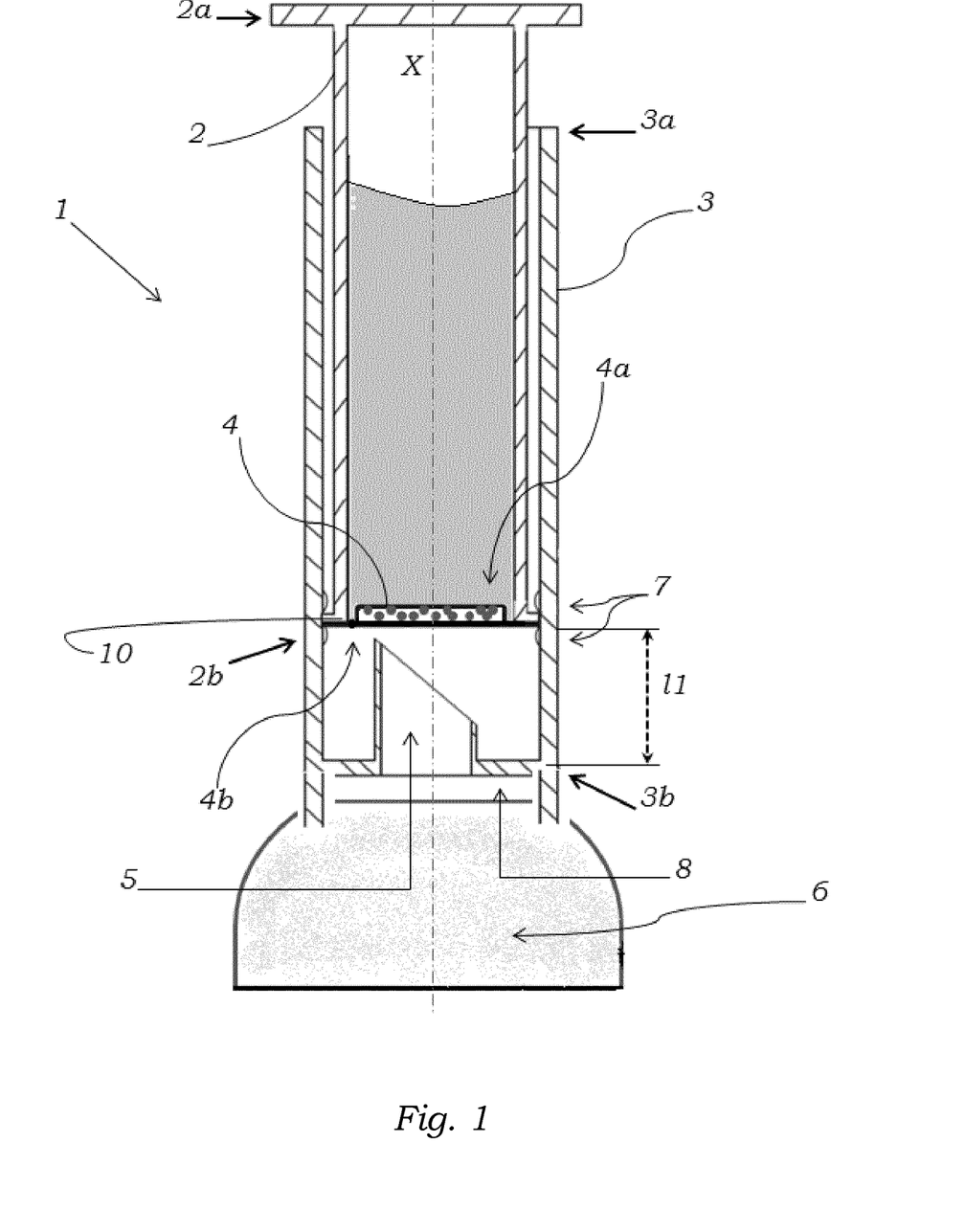
FIG. 1 represents a perspective view of a device for the preparation and application of a medical substance according to the present invention, in an non-activation operating condition, wherein the element of contact with the patient in form of sponge is anchored to the cylindrical chamber.

With reference to FIG. 1, the applicator device comprises a cartridge 2 in form of a hollow container, containing a first medical substance Sa which will be mixed by activating the present applicator device with a second substance Sb contained in the filled double layer 4 as described hereinafter. Regarding this and with reference to FIG. 1, the cartridge 2 has a first end 2a, and a second opposite end 2b, designated to be inserted into the hollow chamber 3.

The first end 2a is external to the hollow chamber 3, and it is shaped so as to allow the movement of the cartridge 2 by applying pressure. In other words, said end 2a may have a solid round or rectangular shape, particularly suitable for promoting the sliding of the cartridge 2 within the chamber 3 for example using the thumb in a fluid and uniform manner. The first end 2a may thus have the protrusions (flanges for example) to increase the grip and ease of use, or it may be provided with a finger grip device of the type known to the person skilled in the art.

In any case, said first end 2a has dimensions such that it is external to the hollow chamber 3 even when the applicator device 1 is activated. By way of example, should the first end 2a be shaped to form a solid disc or ellipse, the diameter thereof would be at least the same as the outer diameter of the hollow chamber 3, preferably greater. In this manner, besides facilitating the exertion of a suitable pressure on said end (condition required for the correct operation of the device 1), it may also serve as a support base, i.e. capable of holding the applicator device 1 in vertical position.

The second end 2b, is instead sealed and it is fully inserted into the hollow chamber 3.

Such end 2b is hermetically closed (sealed) by means of the double layer closure system 4, containing at least one second substance Sb, to be combined with the first substance Sa contained in the cartridge 2. The two substances Sa and Sb, in inoperative conditions of the present applicator device 1, are separated from the layer 4a of the closing system 4, and they come to contact with each other only during the operation of the device 1, i.e. following the tearing of both layers 4a and 4b of the double layer 4, by the breaking systems 5. Typically, in storage conditions, i.e. in inoperative conditions, the cartridge 2 is partly inserted into the hollow chamber 3 through the second sealed end 2b thereof, and held in the temporary blocking position by the means 7.

Regarding this, the outer diameter (or distance) of the cartridge 2 substantially corresponds with the inner diameter (or distance) of the hollow chamber 3, so as to allow the sliding of the cartridge 2 within the hollow chamber 3 in a fluid manner and without lateral leakage of the substance. In an embodiment, the second end 2b has an outer cylindrical collar 10, preferably extended orthogonally with respect to the outer surface of the cartridge 2, and directed towards the inner part of the hollow chamber 3. Said cylindrical collar 10 may have an alternated or even continuous shape and it is mainly meant for stopping the movement of the cartridge 2 upon reaching the end stop position, i.e. the distal end 3b of the hollow chamber 3. Basically, the cylindrical collar 10 extends with respect to the outer surface of the cartridge 2 over a length equivalent to the diameter difference between the outer diameter of the cartridge 2 and the inner diameter of the hollow chamber 3. This allows the sliding of the cartridge 2 in the hollow chamber 3, as required for the correct operation of the device, and also allows stopping the movement of the cartridge 2 upon reaching the distal end 3b of the hollow chamber 3. In addition, said collar 10 allows avoiding the leakage of the medical substance upon activating the device 1, in that it is capable of creating a hermetic sealing even with the end stop, defined by the distal end 3b. Thus, during the operation of the device 1, this latter can even be capsized and for example arranged in a vertical position on the end 2a, without causing the outflow or unwanted and undesired substance leakage. In addition, the cylindrical collar 10 is configured so as to be integrally joined with the temporary blocking means 7 present on the inner surface of the hollow chamber 3, adapted to hold the cartridge 2 stationary after the applicator device has been assembled and is ready for use. In an embodiment, the cartridge 2 contains a liquid medical substance Sa, preferably with antiseptic action, even more preferably containing at least one from among the following active ingredients:

chlorhexidine digluconate, didecyldimethylammonium chloride, benzalkonium chloride, polyhexamethylene biguanide hydrochloride, povidone iodine, isopropyl alcohol, ethyl alcohol or the mixtures thereof. Medical substances Sa in form of aqueous and/or hydroalcoholic solutions of a chlorhexidine salt, even more preferably gluconate, acetate or hydrochloride are particularly preferred. In a further embodiment, the medical substance Sa is an aqueous or hydroalcoholic solution of a chlorhexidine salt, preferably gluconate, mixed with: cetrimide, didecyldimethylammonium chloride, ethanol, hydroxyquinoline or sodium fluoride.

Depending on the type of application and the amount of substance to be applied, the cartridge 2 may have a capacity comprised between about 1 and 100 mL, for example comprised between 2 and 100 mL, preferably cylindrical-shaped.

As regards the hollow chamber 3, it has shapes and dimensions in accordance with those of the cartridge 2 and it has a hosting end 3a adapted to host the cartridge 2, inserted therein through the end 2b thereof, and an open opposite distal end 3b, outside which there is present the contact element 6 with the patient, and from within which the breaking means 5 extends. The hollow chamber 3, has a shape corresponding to that of the cartridge 2, preferably of the hollow cylindrical type, and in this case the inner diameter of the chamber 3 substantially corresponds to the outer diameter of the cylindrical collar 10. The hollow chamber 3 also serves as a means for handling the present applicator device 1 and the outer surface thereof may be provided with anti-slip means, for example in form of reliefs or grooves, adapted to increase and facilitate the grip thereof during the use of the device 1.

Figure 2:
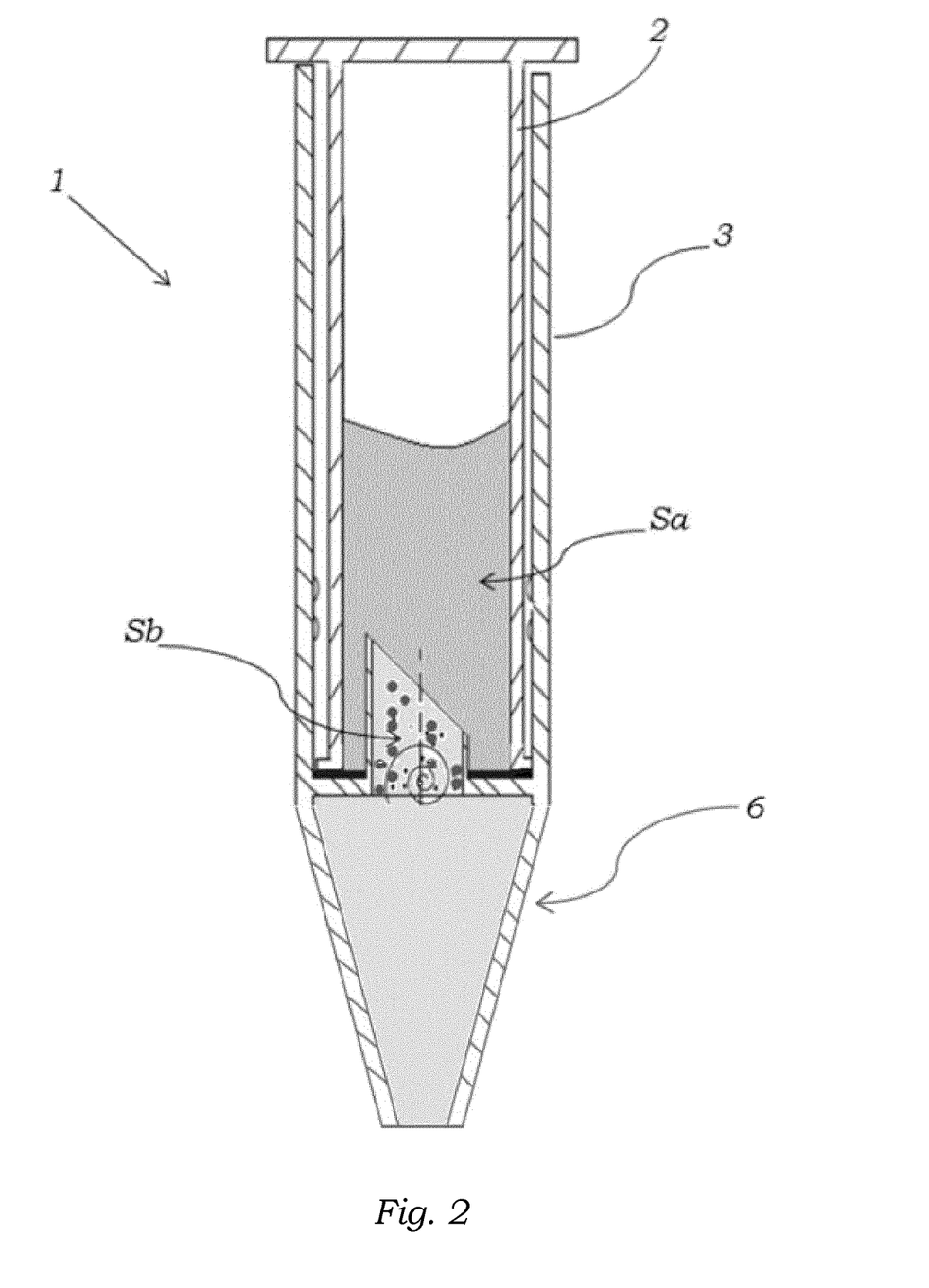
FIG. 2 represents a perspective view of a device for the preparation and application of a medical substance according to the present invention, in an activation operating condition, wherein the element of contact with the patient is in form of an applicator spout.

With reference to FIG. 1 or 2, and as above mentioned, the chamber 3 has temporary blocking means 7 on the inner surface thereof, integrally joined with the cylindrical collar 10. Said blocking means 7 may have shapes and dimensions so that they are capable of obtaining a connection of the reversible coupling type with the cylindrical collar 10. Thus, they may be shaped, for example wedge, uneven and semi-spherical shaped and they substantially serve to hold the cartridge 2 stationary with the applicator device 1 not activated. The blocking condition guaranteed by the means 7 is then unblocked following the activation of the present device 1, i.e. upon exerting a determined pressure on the end 2a of the cartridge 2.

In a preferred embodiment and as illustrated for example in FIG. 1 or 2, the blocking means 7 are positioned in the hollow chamber 3 at a distance 11 from the distal end 3b equivalent to at least the length of the breaking means 5. This allows defining an inner volume of the hollow chamber 3, in which the breaking means 5 is hosted. The sliding distance 11 present between the blocking means 7 and the distal end 3b is sufficient to at least allow the breaking of the filled double layer closure system 4 by means of the breaking means 5, so as to allow the fluid communication between the cartridge 2 and the contact element 6 with the patient, thus making the applicator device 1 of the invention operative. According to such configuration, advantageously, the filled double layer 4 is at the breaking means 5, and it may be rapidly torn by the latter, through a brief sliding movement (distance 11) of the cartridge 2 in the hollow chamber 3, as observable in FIG. 2, thus obtaining an instantaneous mixing of the substances present in the applicator of the invention.

The breaking means 5 is hosted on the distal end 3b and directed towards the internal of the hollow chamber 3. The breaking means 5 is intended to break both layers 4a and 4b forming the filled double layer 4 (according to FIG. 3b), and it also allows the fluid communication between the interior of the cartridge 2 and the contact element 6 with the patient. During the operation of the applicator device 1, the breaking means 5 is actually capable of penetrating into the cartridge 2 breaking both layers 4a and 4b, thus allowing the mixing between the first medical substance Sa (contained in the cartridge 2) and the second substance Sb (contained in the filled double layer 4). When the cartridge 2 reaches the end stop, i.e. the distal end 3b, the breaking means 5 is completely inserted into the cartridge 2, as illustrated by way of example in FIG. 2. Thus, said breaking means 5 is shaped so as to be able to break, by pressing the cartridge 2, the filled double layer 4, in a practical and safe manner, thus facilitating the instantaneous mixing between the medical substance Sa of the cartridge 2 and the medical substance Sb, released from the broken filled double layer. As observable from FIG. 1 or 2, the breaking means 5 extends from the distal end 3b in a preferably orthogonal fashion with respect thereto. The breaking means 5, is also characterised in that it has a hollow shape, preferably cylindrical, even more preferably coaxial with respect to a hypothetical longitudinal axis X throughout the hollow chamber 3. In an embodiment, the breaking means 5 is a spout that is cylindrical-shaped, parallelepiped-shaped or otherwise shaped to form a hollow shape. In a preferred embodiment, the breaking means 5 is a cylindrical or hollow ellipse-shaped spout, having an oblique cutting on the edge, as observable in FIG. 1 or 2. Preferably, said edge has an inclination comprised between about 30° and 60°, even more preferably about 45° with respect to said axis X. Thus, the layers 4a and 4b which are torn following the activation of the present device do not risk occluding the breaking means 5, and they do not negatively interfere with the fluid path. The breaking means 5 is preferably hollow cylindrical-shaped with variable diameter, preferably comprised between 50% and 80% of the interior diameter of the cartridge 2, even more preferably between 60% and 70%.

It should be observed that such configuration not only promotes the fluid communication directly towards the contact element 6 with the patient, but also conveniently facilitates the mixing of the substances Sa and Sb due to the turbulence generated by the release of the substance Sa, as indicated in FIG. 2 by way of example.

The cartridge 2, hollow chamber 3 and breaking means 5 may be made of the same material or even different materials, for example using plastic and/or non-plastic materials usually utilised in the prior art for similar devices. In an embodiment, the components 2, 3 and 5 of the applicator device 1 are made using a material selected from among: polypropylene (PP), polyethylene (PE), high-density polyethylene (HDPE) or the like.

As mentioned above, the breaking means 5 allows the fluid communication between the interior of the cartridge 2 and the contact element 6 with the patient. Generally, the contact element 6 may be any means suitable for the cutaneous administration of the substance prepared with the device of the invention, whether of gel or liquid form. By way of example, the contact element 6 may be in form of a spout (for example as illustrated in FIG. 2), a cylindrical applicator, a roll-on, a porous material, a shaped sponge (for example as illustrated in FIG. 1) or the like. In an embodiment, the element 6 is a material provided with interior cavities open towards the external and mutually communicating, capable of both being impregnated with the final prepared substance in the device 1 following the breaking of the filled double layer 4 as described above, and releasing the same following contact with the patient's skin for example. In this case, the contact element 6 has suitable mechanical and softness characteristics so that it is capable of bearing the mechanical stress caused by the friction with the area of the patient in question, simultaneously avoiding reddening or irritation thereto due to the friction. Preferably, the element 6, is a polyurethane sponge, even more preferably frusto-conical-shaped anchored to the distal end 3b of the hollow chamber 3, as illustrated in FIG. 1 for example. In this case, the contact element 6 encloses both the terminal part of the outer surface of the hollow chamber 3 and the distal end 3b thereof. In particular, the latter is completely enveloped by the element 6 thus creating a soft and smooth application system, without any sharp edges and/or rigid elements. This configuration guarantees homogeneous impregnation of the element 6, so that the surface thereof may be fully exploited by the operator when using the device, thus considerably improving the handling, time and ease of use. As a matter of fact, the soaking of the lateral surface of the contact element 6 guarantees perfect application of the prepared solution with the applicator device of the invention, for example on the skin, through the lateral surface of the element 6, even maintaining the longitudinal axis of the applicator device in a vertical position. The final medical substance prepared with the device 1 is actually not only carried on the lower surface but also radials around the contact element 6. By way of example, in cases where the applicator device 1 contains a first antiseptic substance Sa (for example chlorhexidine digluconate) and a second substance Sb (for example a powder dyeing substance), the device 1 may be used for the identification and disinfection of body areas that are difficult to reach, such as for example the inguinal or underarm areas, maintaining the vertical handling of the applicator, especially due to the special shape and configuration of the contact element 6 in form of a frusto-conical shape.

In order to obtain the particular frusto-conical configuration of the contact element 6, it is preliminarily machined so as to assume a simple cylindrical shape. Preferably, the height of the cylinder represents about half or more of the diameter of the cylinder. Such characteristic shape may be obtained by means of a cut, mechanical machining or preferably starting from polyurethane sheets/rolls. The element thus cylindrical-shaped is positioned at about 90° with respect to the hypothetical longitudinal axis of the hollow chamber 3, so that the two elements are mutually arranged in a coaxial position. The terminal part of the outer surface of the hollow chamber (i.e. the one located at the distal end 3b), or possible purposely designed extensions thereof, is glued, for example with an adhesive glue used in the sector. Alternatively, the distal end 3b may also be wrapped with a special double sided adhesive tape or it may be prepared through possible sealing/polymerisation. Said end is thus inserted into the contact element 6 along the longitudinal axis thereof thus forming the characteristic frusto-conical shape. Thus, the contact element 6 is constantly stretched around the hollow chamber 3. In other words, the element 6, when in form of a sponge, is not in its natural soft and relaxed state but it has a partly deformed and stretched structure facilitating the impregnation thereof and subsequent application of the medical substance prepared with the present applicator device on the skin. As a matter of fact, a relaxed and soft sponge, especially if provided with a considerable profile/height with respect to the diameter, would tend to swell and relax further following the impregnation by the liquid. As a matter of fact, the impregnated sponge has a mass at least 100 times greater than the non-soaked situation. The possible use of a particularly rigid spongy web, which would reduce this effect, would hinder a correct outflow of the liquid and would cause hazardous irritation and abrasion phenomena on the skin.

In an alternative embodiment, for example illustrated in FIG. 2, the contact element 6 may be in form of a protrusion or spout, connected to the distal end 3b of the hollow chamber 3. In this case, the element 6 is particularly adapted for the application of a final substance in form of gel, or however having a high viscosity, such as for example a cream.

In a further embodiment, the element 6 may be stably associated to a solid surface defined by a flange, obtaining shapes and dimensions integrally joined with that of the flange. As a matter of fact, it should be observed that the element 6, may have shapes and angles purposely conceived for particular applications, such as for example the cutaneous treatment of inguinal areas, underarm areas or the like.

According to an embodiment, the contact element 6 has a pre-chamber 8 which facilitates the mixing of the first substance Sa with the second substance Sb. In practice, during the use of the applicator device of the invention, the substance Sa flows from the cartridge 2 towards the contact element 6, passing through the pre-chamber 8. Thus, this creates a turbulence which facilitates the mixing thereof with the substance Sb of the filled double layer 4, thus allowing the preparation of the final medical substance which can thus be applied, as illustrated for example in FIG. 2.

As described above in detail, the activation of the applicator device 1 occurs by exerting pressure on the surface of the upper end 2a of the cartridge 2, external to the hollow chamber 3, up to perforating the filled double layer 4, with the ensuing insertion of the breaking means 5 into the cartridge 2.

Figure 3A:
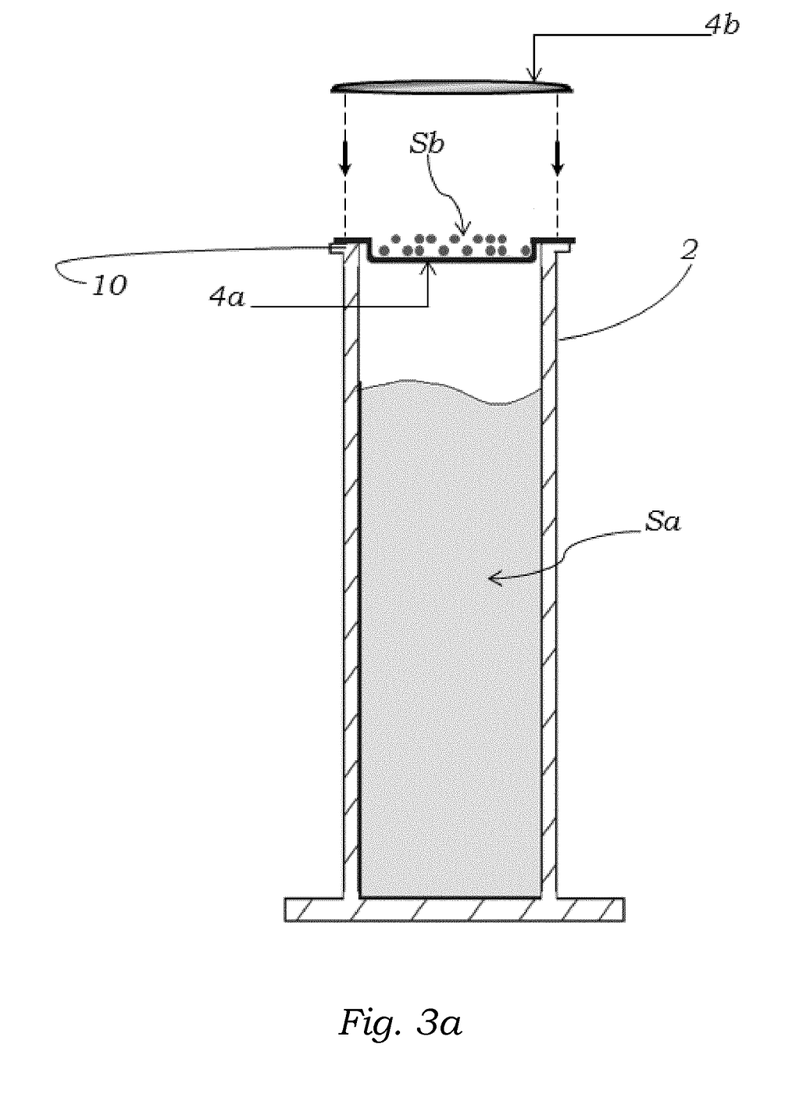
FIG. 3a represents a perspective view, with detached parts, of a detail of a device for the preparation and application of a medical substance according to the present invention.
Figure 3B:
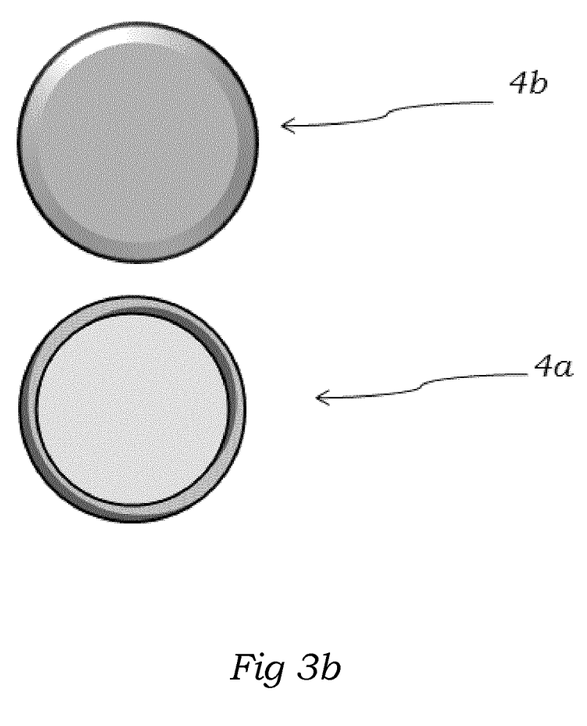
FIG. 3b represents a perspective view, with detached parts, of another detail of a device for the preparation and application of a medical substance according to the present invention.

Regarding this, the filled double layer 4 is formed by a first layer 4b, coupled to a second layer 4a, as illustrated for example in FIGS. 3a and 3b. In this case, the first layer 4b, external to the cartridge 2, also serves as a cap, guaranteeing a hermetic sealing of the cartridge, and the first layer comes to contact with the breaking means 5. The layer 4b extends externally to the cartridge 2 over a length greater than the interior diameter of the cartridge, so as to allow an efficient closure and watertight sealing. Preferably, the first layer 4b extends for a length equivalent to the outer diameter of the cylindrical collar 10, as illustrated in FIG. 3b. The layer 4b is substantially parallel to the end 2b of the cartridge 2 and shaped so as to partly or fully comprise the surface of the circular ring 10, thus serving as a hermetic cap.

The second layer 4a, instead partly extends into the cartridge 2 as illustrated in FIG. 3b. With reference to FIG. 3a, the layer 4a, in particular, has a configuration which allows the anchorage thereof to the cylindrical collar 10, thus allowing the insertion thereof into the cartridge 2. It is apparent that the space for inserting the second layer 4a into the cartridge 2 determines the volume or capacity of the filled double layer 4 which may thus be round or square shaped and it may be more or less deep depending on the required volume.

Figure 4:
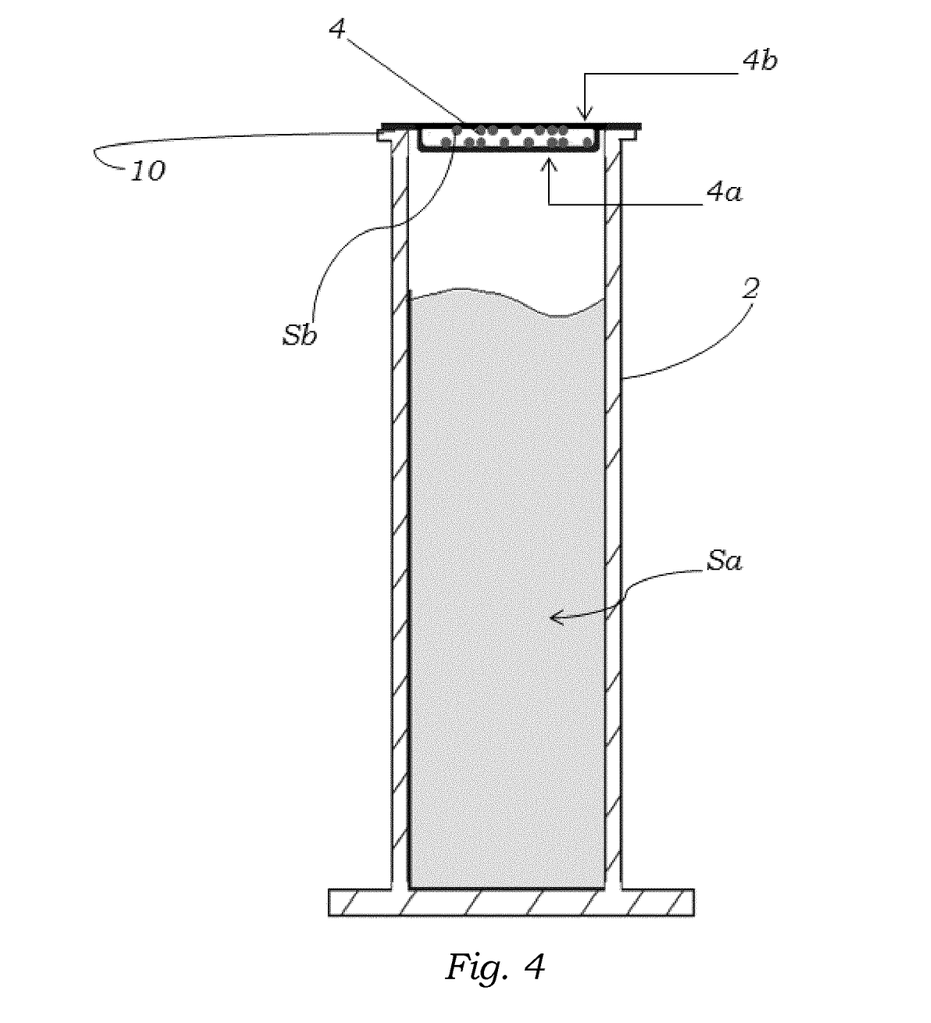

This implies that the layer 4a may be shaped in the cartridge 2 depending on the type and, above all, the amount of substance Sb provided for the insertion into the filled double layer 4, as illustrated in FIG. 4. By way of example, the volume formed by the two layers 4b and 4a may be obtained so as to contain the amount of a dyeing substance Sb, required for combining with a substance Sa, for example an antiseptic solution, typically depending on the desired intensity of the dyeing of the final substance, and the amount of substance Sa to be mixed. Regarding this, in a preferred embodiment, the filled double layer 4, may contain a medical and/or dyeing substance Sb in liquid, paste, gel or preferably powder form. In an embodiment, the filled double layer 4 contains a dyeing substance in form of powder or granules, gel or paste, i.e. capable of conferring a cutaneous colouring, for mixing with the medical substance Sa contained in the cartridge 2, and obtain a final dyeing substance efficiently utilisable in the medical industry. In an embodiment, the dyeing substance contained in the filled double layer 4 is at least one selected from among: azorubine, methylene blue (3,7-bis-(dimethylamino) phenazathionium (CAS N. 61-73-4)), patent blue (in form of sodium salt (CAS 20262-76-4) or calcium salt (CAS 3536-49-0).

In an equally preferred embodiment, the filled double layer 4 may contain, additionally or alternatively to the dyeing substance, a second medical substance Sb1 such as for example an active ingredient, preferably with an antiseptic and/or disinfectant and/or antibacterial action. Thus, should the substance Sa contained in the cartridge 2 also be an antiseptic agent, the action of the two substances Sa and Sb1 may be combined thus obtaining a device 1 for the preparation and administration of a final antiseptic substance with wide range of action and high efficiency, specifically due to the combination (even synergic) of the two substances Sa and Sb1.

The layers 4b and 4a have the characteristics and dimensions which allow the breaking thereof following contact with the breaking means 5, as described above in detail. By way of example, they may be obtained using an aluminium film by means of heat sealing coupled to PE and PP, or coupled or co-extruded films based on polymeric materials (such as for example polyethylene terephthalate (PET), polyethylene (PE), ethylene vinyl alcohol (EVOH), polypropylene (PP). The layers 4b and 4a are mutually heat sealed to each other or glued or sealed through other methods such as high frequency.

The method for the preparation of the applicator device 1 comprises the initial filling of the cartridge 2 with the desired amount of at least one first medical substance Sa. The cartridge thus filled is thus sealed using the second shaped layer 4a of the filled double layer 4 by anchoring said layer to the cylindrical collar 10, for example by gluing. Thus, there follows the dosage of at least one second substance Sb and/or Sb1 in the shaped layer 4a, and the subsequent positioning of the first layer 4b with the sealing closure of the cartridge 2, as illustrated in FIGS. 3a and 4. The cartridge 2 is thus ready to be partly inserted into the hollow chamber 3, up to the coupling of the end 2b with the partial blocking means 7.

As clear from the description outlined above, it should be observed that the extreme versatility and ease of assembly as well as use of the present dosing device 1 allow using medical substances that can be both active ingredients and dyeing or neutral substances. Besides the preferred embodiment according to which the cartridge 2 comprises an antiseptic substance Sa and the filled double layer 4 contains a dyeing substance Sb and/or Sb1 as described above, the dosing device 1 may be configured so that the substances Sa and Sb and/or Sb1 be inverted with respect to each other, for example using a dyeing substance in the cartridge (such as water mixed with a dyeing substance) and a medical substance or active ingredient in the filled double layer. Such versatility advantageously allows utilising the present applicator device in an extremely high number of medical applications, both preoperative and post-operative or curative interventions in general. Besides the type of utilisable substances, it should be observed that the dosage thereof may be optimised in that the filled double layer 4, once the device is operative, does not retain part of the content thereof, such as for example in the case of similar devices of the prior art in which a filter, a porous septum, or an impregnation system is used. The use of colouring filters through which the antiseptic solution becomes coloured may actually not guarantee an accurate dosage of the amount of impregnated powder, contrary to the filled double layer system described in the present invention.

Thus, the device 1 for the preparation and application of at least one medical substance is particularly useful in cases where it is required to prepare a chemically unstable final substance whereby its application is carried out shortly after the preparation thereof. In particular, some antiseptic substances may reveal instability problems when mixed with dyeing substances. Thanks to the present invention, it is now possible to prepare substantially any type of coloured antiseptic substance, by introducing the medical substance into the cartridge, and separately, the dyeing substance into the filled double layer 4. Thus, when the device is inoperative, the two substances do not come to contact with each other, thus maintaining their chemical nature unaltered. As a matter of fact, the use of the device 1, allows the dyeing substance and the active ingredient to come to contact with each other only when required thus allowing the preparation of the final coloured medical substance which is thus applied to the skin of the patient through the suitable contact element 6.

The invention claimed is:

1. Applicator device for preparing and applying at least one medical substance, the applicator device comprising: a hollow chamber having one hosting end and an opposite distal end in communication with a means for contacting a patient;
   a cartridge slidably inserted inside said hollow chamber by means of the hosting end, containing at least one first medical substance, having a first end external to the hollow chamber, and a second end completely inserted into the hollow chamber and having an outer circular collar, extended orthogonally with respect to the outer surface of the cartridge, and directed towards the inner part of the chamber;
   a breaking means positioned at the distal end capable of establishing a fluid communication between the interior of the cartridge and the means for the contact with a patient;
   said second end being characterized in that it is closed by a filled double layer closure system containing at least a second medical substance mixable and/or soluble with said first medical substance, wherein said filled double layer closure system is obtained by coupling a first layer and a second layer, wherein said first layer extends for a length equal to the outer diameter of the circular collar, acting as a hermetic cap, and said second layer partially extends inside the cartridge, said first layer and second layer defining an internal volume containing said second medical substance.

2. Applicator device according to claim 1, wherein the first medical substance has an antiseptic activity.

3. Applicator device according to claim 2, wherein said first medical substance having an antiseptic activity is selected from: chlorhexidine, didecyldimethylammonium chloride, benzalkonium chloride.

4. Applicator device according to claim 1, wherein said filled double layer closure system contains at least one dyeing substance in the form of a powder.

5. Applicator device according to claim 1, wherein said breaking means has a cutting edge inclined by an angle comprised between 30° and 60° with respect to a hypothetical longitudinal axis X passing through the hollow chamber.

6. Applicator device according to claim 5, wherein said breaking means has a cylindrical shape, coaxial with respect to said longitudinal axis X.

7. Applicator device according to claim 1, wherein said first layer is shaped so as to comprise part or a whole surface of the circular collar.

8. Applicator device according to claim 1, wherein said first layer and/or said second layer are made with aluminium or with a polymeric material, and heat sealed or glued to each other.

9. Applicator device according to claim 1, further comprising temporary blocking means, located on the inner surface of the hollow chamber capable of achieving a reversible coupling with the circular collar.

10. Applicator device according to claim 9, wherein said temporary blocking means are positioned on the inner surface of the hollow chamber at a distance from the distal end equal to at least the length of the breaking means.

11. Applicator device according to claim 1, wherein said means for contacting a patient is an applicator means suitable for cutaneous administration of a final substance prepared using the device, said means for contacting a patient being in the form of a spout, a cylindrical applicator, a roll-on device, a porous material or a shaped sponge.

12. Applicator device according to claim 1, wherein said at least one medical substance is a colored liquid.

13. Applicator device according to claim 3, wherein said medical substance having an antiseptic action is an aqueous or hydroalcoholic solution of a chlorhexidine salt selected from: gluconate, acetate and hydrochloride.

* * * * *